United States Patent [19]

De Graaff et al.

[11] Patent Number: 5,681,732
[45] Date of Patent: Oct. 28, 1997

[54] CLONING AND EXPRESSION OF ACETYL XYLAN ESTERASES FROM FUNGAL ORIGIN

[75] Inventors: Leendert H. De Graaff, Oosterbeek; Jacob Visser, Wageningen; Henriette C. Van Den Broeck, Ede, all of Netherlands; Francois Strozyk, Leforest, France; Felix J. M. Kormelink, Bennekom; Johannes C. P. Boonman, Haarlem, both of Netherlands

[73] Assignee: Gist-brocades, B.V., Netherlands

[21] Appl. No.: 291,609

[22] Filed: Aug. 17, 1994

Related U.S. Application Data

[63] Continuation of Ser. No. 851,976, Mar. 16, 1992, Pat. No. 5,426,043.

[30] Foreign Application Priority Data

Mar. 18, 1991 [EP] European Pat. Off. .............. 91200579

[51] Int. Cl.⁶ .............. C12N 15/55; C12N 9/18; C12N 1/15; C12N 15/63
[52] U.S. Cl. .............. 435/197; 435/69.1; 435/71.2; 435/252.3; 435/252.31; 435/320.1; 435/172.3; 435/254.2; 435/254.3; 536/23.2; 935/14; 935/29; 935/56
[58] Field of Search .............. 435/69.1, 71.2, 435/197, 252.3, 252.31, 320.1, 172.3, 254.2, 254.3; 536/23.2; 935/14, 29, 56

[56] References Cited

PUBLICATIONS

A. W. Khan et al. Enzyme Microb. Tecnol. 12:127–131 (Feb. 1990).
Beily et al Can J. Microbiol 34(6) 767–772 (1988).
Sundberg et al Biotechnol Appl. Biochem 13(1) 1–11 (1991).
A. Belyansky et al. Nuc. Acids. Res. 17(8) 2919–2932 (Apr. 1989).
S. L. Berger et al. "Guide to Molecular Cloning Techniques" Meth. in Enzymol. 152:393–399, 415–423, 432–447, 661–704 (1987).
M. P. Deutscher "Guide to Protein Purification" Meth. in Enzymol. 182: 602–613, 738–751 (1990).
Poutanen et al., *Applied Microbiology and Biotechnology* (1990) 33:506–510.
Biely et al., *FEBS Letters* (1985) 186(1):80–84.
Grohmann et al., *Applied Biochemistry and Biotechnology* (1989) 20/21:45–61.

*Primary Examiner*—Robert A. Wax
*Assistant Examiner*—Rebecca Prouty
*Attorney, Agent, or Firm*—Morrison & Foerster LLP

[57] ABSTRACT

Methods and DNA constructs are provided for the expression of a fungal acetyl xylan esterase gene in microbial hosts. A purified fungal acetyl xylan esterase is obtained which is suited for the use as an accessory enzyme in the degradation of acetylated xylans.

16 Claims, 2 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear (  i i  ) MOLECULE TYPE: peptide (  x i  ) SEQUENCE DESCRIPTION: SEQ ID NO:1:

Ser  Gly  Ser  Leu  Gln  Gln  Val  Thr  Asp  Phe  Gly  Asp  Asn  Pro  Thr  Asn
1                 5                             10                              15

Val  Gly  Met  Tyr  Ile
               20

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

Tyr  Ile  Tyr  Val  Pro  Asn  Asn  Leu  Ala  Ser  Asn  Pro  Gly  Ile  Val  Val
1                 5                             10                              15

Ala  Ile  His  Tyr
               20

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified-site
        ( B ) LOCATION: 1
        ( D ) OTHER INFORMATION: /note= "This position is ?."

( i x ) FEATURE:
        ( A ) NAME/KEY: Modified-site
        ( B ) LOCATION: 11
        ( D ) OTHER INFORMATION: /note= "This position is
        ( H i s / T h r )."

( x i ) SEQUENCE DESCRIPTION: SEQ ID NO:3:

Xaa  Ser  Gly  Tyr  Ser  Gly  Ser  Phe  Pro  Thr  Xaa  Gln  Ile  Tyr  Xaa  Ser
1                 5                             10                              15

Gly  Ser  Ser  Asp
               20

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 9
        ( D ) OTHER INFORMATION: /note= "This position is I."

( i x ) FEATURE:
        ( A ) NAME/KEY: misc_feature
        ( B ) LOCATION: 18
        ( D ) OTHER INFORMATION: /note= "This position is I."

( i x ) FEATURE:

( A ) NAME/KEY: misc_feature
                    ( B ) LOCATION: 21
                    ( D ) OTHER INFORMATION: /note= "This position is I."

( x i ) SEQUENCE DESCRIPTION: SEQ ID NO:4:

GGATTATCNC CAAAATCNGT NACCTGCTG                                                29

( 2 ) INFORMATION FOR SEQ ID NO:5:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: misc_difference
                    ( B ) LOCATION: replace(9, "")
                    ( D ) OTHER INFORMATION: /note= "This position is I."

( i x ) FEATURE:
                    ( A ) NAME/KEY: misc_difference
                    ( B ) LOCATION: replace(12, "")
                    ( D ) OTHER INFORMATION: /note= "This position is I."

( x i ) SEQUENCE DESCRIPTION: SEQ ID NO:5:

CCAAAATCNG TNACTTGTTG                                                          20

( 2 ) INFORMATION FOR SEQ ID NO:6:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: misc_feature
                    ( B ) LOCATION: 6
                    ( D ) OTHER INFORMATION: /note= "This position is I."

( i x ) FEATURE:
                    ( A ) NAME/KEY: misc_feature
                    ( B ) LOCATION: 9
                    ( D ) OTHER INFORMATION: /note= "This position is I."

( x i ) SEQUENCE DESCRIPTION: SEQ ID NO:6:

TTATTNGGNA CATAGATATA                                                          20

( 2 ) INFORMATION FOR SEQ ID NO:7:

( i ) SEQUENCE CHARACTERISTICS:
                    ( A ) LENGTH: 1943 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: TATA_signal
                    ( B ) LOCATION: 606..612

( i x ) FEATURE:
                    ( A ) NAME/KEY: CAAT_signal
                    ( B ) LOCATION: 534..538
                    ( D ) OTHER INFORMATION: /note= "CCAAT box."

( i x ) FEATURE:
                    ( A ) NAME/KEY: CDS (B) LOCATION: join(713..917, 971..1227, 1306..1755)

(ix) FEATURE:
    (A) NAME/KEY: misc_feature
    (B) LOCATION: 713..787
    (D) OTHER INFORMATION: /note= "From 713 to 800 prepropeptide."

(ix) FEATURE:
    (A) NAME/KEY: mat_peptide
    (B) LOCATION: join(788..917, 971..1227, 1306..1756)

(xi) SEQUENCE DESCRIPTION: SEQ ID NO:7:

```
AAATATGTCT TTTATTACCT TGTTCTGTTG ACTGGTGCAT TACTTAAAAC TAGAACAGTT      60
GTTCAAACAC AAGTTGGACC TATACCTGTC ATAACTCGCC TCGTCGCGTT ATTCATCATG     120
CAAAAACTAT CCGTTATCAG CGCCGGGAGT ATACTCCCAA GAAGCTCACT CACATGCAAA     180
GAAATGTGCC GATTGCTTAA GCTTACCCC AGATTATTCC GTAACCATAT ATCCATTCTG      240
GCTGAATACC GGCTATTTGA TGCTGCATAC TCTCACATTC CGCACAGCCG CCAGTGTGAA     300
GAATCACCAG TGGTCCAGCC CTGCAGTGGC TCTAACGGGA TCTGTTACGG AGTTCGGCCC     360
GCAACGTCGA TCTCTAACCA TTTCGATCTG GAGTTCCCAC TCCGTGCCGT CTATCCCAGA     420
CTCCTCATGT CGGAGCTGTC ACGGCTGTCA CATTAGCCCT GCTTAATTTC CGTGATGAAA     480
TCAGCCTACA CTGTCATTTC TATGTCTAGA CCACTGCCAA ATACCCACTG AACCCAATAC     540
TTCCCACAAC TATAGAAACA TACTATTACT CCATAATGTT TCAATTTACC CGCTCTCTGC     600
AGCGCTATAA ATCGTCTTCA AATCCTCTGG CGTCTTTCCT ACTGCCCAAG CTGCATCTCT     660
TTTCACCTAG CAGGATTCAA GCGTAGTGCC TAGCACGGCA GAAGAAACCA CC ATG         715
                                                         Met
                                                          1

CTA CTA TCA ACC CAC CTC CTC TTC GTC ATC ACC ACC TTC TTA ACC TCC      763
Leu Leu Ser Thr His Leu Leu Phe Val Ile Thr Thr Phe Leu Thr Ser
          5                  10                  15

CTC CTC CAC CCC ATC GCC GCC CAT GCT GTC AAG CGC AGT GGC AGT CTT      811
Leu Leu His Pro Ile Ala Ala His Ala Val Lys Arg Ser Gly Ser Leu
             20                  25                  30

CAA CAG GTC ACC GAT TTC GGT GAC AAC CCT ACA AAT GTA GGC ATG TAC      859
Gln Gln Val Thr Asp Phe Gly Asp Asn Pro Thr Asn Val Gly Met Tyr
     35                  40                  45

ATC TAC GTG CCT AAC AAC TTG GCC TCA AAT CCA GGT ATC GTG GTT GCA      907
Ile Tyr Val Pro Asn Asn Leu Ala Ser Asn Pro Gly Ile Val Val Ala
 50                  55                  60                  65

ATC CAC TAC T GTACGTTCCC CCACATTTCT ACAATATAAA CCACAATACT            957
Ile His Tyr

AAGCATGGCA TAG GC ACC GGT ACC GGC CCC GGC TAC TAC AGC GCC TCC       1005
              Cys Thr Gly Thr Gly Pro Gly Tyr Tyr Ser Ala Ser
                         70                  75                  80

CCC TAC GCC ACC CTC TCC GAG CAA TAC GGC TTT ATC GTG ATC TAC CCG     1053
Pro Tyr Ala Thr Leu Ser Glu Gln Tyr Gly Phe Ile Val Ile Tyr Pro
             85                  90                  95

TCC AGC CCA TAC TCC GGT GGC TGT TGG GAC GTG AGT TCA CAG GCA ACG     1101
Ser Ser Pro Tyr Ser Gly Gly Cys Trp Asp Val Ser Ser Gln Ala Thr
            100                 105                 110

TTA ACA CAC AAC GGG GGC GGA AAC AGT AAC TCC ATT GCC AAC ATG GTC     1149
Leu Thr His Asn Gly Gly Gly Asn Ser Asn Ser Ile Ala Asn Met Val
            115                 120                 125

ACC TGG ACG ATT AGC GAG TAC GGG GCC GAT AGT AGC AAG GTG TTC GTG     1197
Thr Trp Thr Ile Ser Glu Tyr Gly Ala Asp Ser Ser Lys Val Phe Val
        130                 135                 140

ACG GGA TCG AGT TCG GGG GCT ATG TTG ACG GTATTCCTC TTCCCTTCCA        1247
```

```
Thr Gly Ser Ser Ser Gly Ala Met Leu Thr
145                 150
```

| | | | | | |
|---|---|---|---|---|---|
| ACCGTTCCCC | CTCTCTACAA | ATTAAAATAG | TAAAAGTTGT | GCATGCTAAT | AAAATTAG | 1305 |

```
AAC GTA ATG GCA GCA ACC TAC CCC GAA CTC TTC GCC GCC GCC ACC GTC    1353
Asn Val Met Ala Ala Thr Tyr Pro Glu Leu Phe Ala Ala Ala Thr Val
155             160                 165                 170

TAC TCC GGA GTC TCA GCC GGG TGC TTC TAC TCG AAC ACC AAC CAA GTA    1401
Tyr Ser Gly Val Ser Ala Gly Cys Phe Tyr Ser Asn Thr Asn Gln Val
                175                 180                 185

GAT GGA TGG AAT TCC ACT TGC GCC CAG GGT GAT GTA ATC ACC ACC CCC    1449
Asp Gly Trp Asn Ser Thr Cys Ala Gln Gly Asp Val Ile Thr Thr Pro
            190                 195                 200

GAG CAC TGG GCC AGT ATT GCA GAG GCA ATG TAC TCG GGA TAC TCA GGA    1497
Glu His Trp Ala Ser Ile Ala Glu Ala Met Tyr Ser Gly Tyr Ser Gly
        205                 210                 215

AGT CGT CCA AGG ATG CAG ATC TAC CAC GGT ACT CTC CAT ACG ACG CTG    1545
Ser Arg Pro Arg Met Gln Ile Tyr His Gly Thr Leu His Thr Thr Leu
    220                 225                 230

TAT CCT CAG AAC TAC TAT GAG ACG TGC AAG CAG TGG TCT GGA GTG TTT    1593
Tyr Pro Gln Asn Tyr Tyr Glu Thr Cys Lys Gln Trp Ser Gly Val Phe
235                 240                 245                 250

GGA TAT GAT TAT AGC GCA CCG GAG AAG ACG GAG GCG AAT ACC CCA CAG    1641
Gly Tyr Asp Tyr Ser Ala Pro Glu Lys Thr Glu Ala Asn Thr Pro Gln
                255                 260                 265

ACG AAT TAC GAG ACG ACG ATT TGG GGA GAT AGT CTG CAG GGA ATC TTC    1689
Thr Asn Tyr Glu Thr Thr Ile Trp Gly Asp Ser Leu Gln Gly Ile Phe
            270                 275                 280

GCG ACA GGC GTG GGT CAT ACG GTG CCG ATT CAT GGG GAT AAG GAT ATG    1737
Ala Thr Gly Val Gly His Thr Val Pro Ile His Gly Asp Lys Asp Met
        285                 290                 295

GAG TGG TTT GGG TTT GCT TGATTGGATG ATCGAATGGT TTAGCCTGGG           1785
Glu Trp Phe Gly Phe Ala
300
```

| | | | | | |
|---|---|---|---|---|---|
| GGTATCTCGG | AACCGGGAAT | GATGAAACTT | CTGAAGTATG | ATATGTTAAC | GATATCGCGT | 1845 |
| CAACGAGCGT | TGTTGAAGC | TTTAGTGTGT | AATGTGGAGT | ATGAGCAAAA | TGTGCGCTGC | 1905 |
| CCGTGTCTGA | TGCCAAAACC | AATGCAGCAC | AAGAGCTC | | | 1943 |

( 2 ) INFORMATION FOR SEQ ID NO:8:

( i ) SEQUENCE CHARACTERISTICS:
      ( A ) LENGTH: 304 amino acids
      ( B ) TYPE: amino acid
      ( D ) TOPOLOGY: linear ( i i ) MOLECULE TYPE: protein ( x i ) SEQUENCE DESCRIPTION: SEQ ID NO:8:

```
Met Leu Leu Ser Thr His Leu Leu Phe Val Ile Thr Thr Phe Leu Thr
1               5                   10                  15

Ser Leu Leu His Pro Ile Ala Ala His Ala Val Lys Arg Ser Gly Ser
                20                  25                  30

Leu Gln Gln Val Thr Asp Phe Gly Asp Asn Pro Thr Asn Val Gly Met
            35                  40                  45

Tyr Ile Tyr Val Pro Asn Asn Leu Ala Ser Asn Pro Gly Ile Val Val
    50                  55                  60

Ala Ile His Tyr Cys Thr Gly Thr Gly Pro Gly Tyr Tyr Ser Ala Ser
65                  70                  75                  80

Pro Tyr Ala Thr Leu Ser Glu Gln Tyr Gly Phe Ile Val Ile Tyr Pro
                85                  90                  95
```

```
Ser  Ser  Pro  Tyr  Ser  Gly  Gly  Cys  Trp  Asp  Val  Ser  Ser  Gln  Ala  Thr
               100            105                      110
Leu  Thr  His  Asn  Gly  Gly  Gly  Asn  Ser  Asn  Ser  Ile  Ala  Asn  Met  Val
          115                 120                      125
Thr  Trp  Thr  Ile  Ser  Glu  Tyr  Gly  Ala  Asp  Ser  Ser  Lys  Val  Phe  Val
     130                      135                 140
Thr  Gly  Ser  Ser  Ser  Gly  Ala  Met  Leu  Thr  Asn  Val  Met  Ala  Ala  Thr
145                      150                 155                           160
Tyr  Pro  Glu  Leu  Phe  Ala  Ala  Ala  Thr  Val  Tyr  Ser  Gly  Val  Ser  Ala
                    165                      170                      175
Gly  Cys  Phe  Tyr  Ser  Asn  Thr  Asn  Gln  Val  Asp  Gly  Trp  Asn  Ser  Thr
               180                      185                      190
9
Cys  Ala  Gln  Gly  Asp  Val  Ile  Thr  Thr  Pro  Glu  His  Trp  Ala  Ser  Ile
          195                      200                      205
Ala  Glu  Ala  Met  Tyr  Ser  Gly  Tyr  Ser  Gly  Ser  Arg  Pro  Arg  Met  Gln
     210                      215                      220
Ile  Tyr  His  Gly  Thr  Leu  His  Thr  Thr  Leu  Tyr  Pro  Gln  Asn  Tyr  Tyr
225                           230                      235                 240
Glu  Thr  Cys  Lys  Gln  Trp  Ser  Gly  Val  Phe  Gly  Tyr  Asp  Tyr  Ser  Ala
               245                      250                      255
Pro  Glu  Lys  Thr  Glu  Ala  Asn  Thr  Pro  Gln  Thr  Asn  Tyr  Glu  Thr  Thr
               260                      265                      270
Ile  Trp  Gly  Asp  Ser  Leu  Gln  Gly  Ile  Phe  Ala  Thr  Gly  Val  Gly  His
          275                 280                      285
Thr  Val  Pro  Ile  His  Gly  Asp  Lys  Asp  Met  Glu  Trp  Phe  Gly  Phe  Ala
     290                      295                      300
```

CLONING AND EXPRESSION OF ACETYL XYLAN ESTERASES FROM FUNGAL ORIGIN

This application is a continuation of application Ser. No. 07/851,976 filed 16 Mar. 1992 now U.S. Pat. No. 5,426,043.

TECHNICAL FIELD

The present invention relates to the field of molecular biology. In particular, the invention relates to the cloning and expression of a DNA sequence encoding a fungal acetyl xylan esterase. The present invention provides a recombinant acetyl xylan esterase obtained by expression of the cloned DNA sequence encoding this protein. The protein thus obtained is used in xylan degradation in feed or pulp.

BACKGROUND OF THE INVENTION

The rigid structure of cell walls of plant tissues is due to xylans together with other hemicelluloses, pectins, cellulose and lignin. Xylans form the major hemicellulose, most xylans are heteropolysaccharides with a homopolymeric backbone chain of 1,4-linked β-D-xylopyranose units. The plant of origin determines the degree and the type of substitutions of the specific xylan. Xylans are found to contain many different side groups, among these L-arabinose, D-glucuronic acid or its 4-O-methyl ether, and acetic, p-coumaric, and ferulic acids are the most prominent.

It has been suggested that both acetyl and arabinosyl substituents increase the solubility of hemicellulose by decreasing the possibility of intermolecular aggregation, however, these substituents are at the same time a severe hindrance to the enzymatic degradation of the plant tissues. For example, it has been reported that acetylation inhibits the digestibility of plant polysaccharides in ruminants. Poutanen and Puls (1989) (In Biogenesis and Biodegradation of Plant Cell Wall Polymers (Lewis, N. and Paice, M. eds) ACS Symp. Ser. 399: 630–640), have shown that the major xylanase of *Trichoderma reesei* is unable to depolymerize acetylated soluble xylan. Grohmann et al. (1989) (Appl. Biochem. Biotechnol. 20/21: 45–61) have shown that after chemical deacetylation xylan is 5–7 times more digestible by ruminants.

Esterases (EC 3.1.1.6) are classified according to their substrate specificity. Since it is generally difficult to determine the natural substrate for these enzymes the classification is problematic and this problem is enlarged by the widespread appearence of esterases in nature. It is therefore not surprising that although the existence of enzymes that deacetylate xylan may have been anticipated in view of the long known occurrence of microbial esterases that were known to act on various synthetic substrates, it was not until recently that the existence of acetyl xylan esterases was demonstrated.

Biely et al. (1985, FEBS Lett. 186: 80–84) demonstrated the presence of acetyl xylan esterases in (fungal) cellulolytic and hemicellulolytic systems: *Trichoderma reesei, Aspergillus niger, Schizophyllum commune* and *Aureobasidium pullulans*. As compared with plant and animal esterases, these fungal esterases exhibit high specific activities towards acetylated glucuronoxylan and were therefore named acetyl xylan esterases.

Further investigations on the fungal acetyl esterases have been reported. Poutanen et al. (1988, Appl. Microbiol. Biotechnol. 28: 419–425 and 1990, Appl. Microbiol. Biotechnol. 33: 506–510) described the purification and characterization of acetyl xylan esterases from *T. reesei*. Enzymatic deacetylation of xylan using purified acetyl xylan esterass resulted in the precipitation of the remaining polymer structure. Due to this effect acetyl esterase is not used as a single first enzyme in the degradation of acetylated xylans. The highest xylose yield from acetylated xylan was obtained by the synergistic action of xylanase, β-xylosidase and acetyl xylan esterase.

To achieve a practically useful degradation of xylans there is a need for large amounts of the enzymes involved in the enzymatic hydrolysis of these highly substituted molecules. The present invention provides a way for obtaining large amounts of fungal acetyl xylan esterases, optionally in a purified form.

SUMMARY OF THE INVENTION

It is an object of the present invention to provide a purified and isolated acetyl xylan esterase of fungal origin. This protein is the expression product of the gene encoding a fungal acetyl xylan esterase.

The present invention further provides constructs for the microbial expression of the acetyl xylan esterase-encoding sequence using either its native regulatory sequences or, in an alternative embodiment, using the gene operatively coupled to regulatory regions such as promoter, secretion leader and terminator signals selected depending on the desired expression host.

It is a further object of the present invention to provide expression hosts, transformed with the expression constructs of the present invention, which are capable of the overexpression and, if desired, the secretion of the acetyl xylan esterase of fungal origin.

It is yet a further object of the present invention to provide methods for the production of large quantities of an acetyl xylan esterase.

Furthermore the present invention provides a method for increasing feed digestibility characterized in that an effective amount of acetyl xylan esterase is added to the feed. The present invention also provides a method for decreasing the viscosity of xylan containing compositions characterized in that an effective amount of acetyl xylan esterase is added.

The present invention also provides a method for the release of lignin from kraft pulp in the preparation of paper products.

DETAILED DESCRIPTION OF THE INVENTION

Filamentous fungi are widely known for their capacity to secrete large amounts of a variety of hydrolytic enzymes such as α-amylases, proteases and glucoamylases, and various plant cell wall degrading enzymes such as cellulases, hemi-cellulases, and pectinases.

The present invention describes a purified and isolated DNA molecule comprising the sequence of an acetyl xylan esterase gene of fungal origin and genetic variants thereof. Genetic variants are those DNA sequences encoding mutant acetyl xylan esterases. Also encompassed by the present invention are fungal DNA sequences that hybridize with the presented sequences under stringent conditions and that upon expression give rise to a protein which shows, esterase activity. Specifically the *A. niger* acetyl xylan esterase gene, isolated in one of the examples, was shown to hybridize with *T. reesei* chromosomal DNA.

The present invention also pertains to homologous or heterologous hosts transformed by recombinant DNA molecules containing the DNA sequences described above. With "homologous host" is intended the species from which the gene is obtained. "Heterologous host" pertains to hosts other than the source from which the gene is obtained. Heterologous hosts may be selected from bacteria, yeasts or fungi. The terms homologous and heterologous are also used with respect to the regulating sequences. In this case "homologous" refers to the regulating sequences which are native to the cloned gene and "heterologous" to regulating sequences from other genes or from the same gene obtained from another species.

Acetyl xylan esterases of particular interest are those which are obtained from fungi of the genera Aspergillus, Trichoderma, Schizophyllum. Preferred species are *Trichoderma reesei, Aspergillus niger* and *Schizophyllum commune*.

Fungi showing acetyl xylan esterase activity can be used to isolate the protein by methods well-known in the art. In the presented examples *Aspergillus niger* is used as the source of the acetyl xylan esterase.

The acetyl xylan esterase is produced by culturing the Aspergillus strain. The protein is purified by known methods and the yield of the purification is followed by a suitable activity assay.

As a first step of the characterisation of the protein structure a part of the amino acid sequence of the isolated protein is determined. When N-terminal amino acid sequencing techniques are used this can be the N-terminal part of the mature protein, but this can also be the N-terminus of an internal peptide obtained after digestion of the purified protein with a specific proteinase such as trypsin, chymotrypsin etc or with a chemical reagent e.g. CNBr. When using C-terminal sequencing methods it is possible to determine C-terminal sequences of the protein or peptides. Once such a sequence is known it is possible to derive a nucleotide probe based on this sequence. Preferably this probe is devised against a part of the protein which contains amino acids which are encoded by codons that show little degeneracy.

The probes that are obtained in such a way can be labeled and used to hybridize with the clones from a cDNA or genomic library. From the clones showing a positive hybridization signal the vector is isolated and the nucleotide sequence of the insert is determined. Hybridisation and sequencing can be repeated if no full length clone is found. Full-length clones can also be obtained by combining overlapping restriction fragments all encoding a part of the desired protein sequence. The obtained DNA sequence can be cloned in appropriate expression vectors. Where appropriate is related to the choice of the expression host organism. This cloning can also be performed without determination of the nucleotide sequence, however, this will probably give rise to a non-optimal construct. Preferred expression hosts can be bacteria, yeasts or fungi. Specifically Kluyveromyces, Bacillus, Aspergillus or *E. coli* are used.

To regulate the expression, regulatory regions are cloned in such a way that the gene is operationally linked with them.

Among these regulatory regions homologous and heterologous promoters, operators, enhancers, signal sequences and ribosomal binding sites can be used. Furthermore, the gens can be cloned on a self-replicating vector or it can be integrated into the genome of the host organism, preferably more copies of the gene are used.

Finally, the obtained gene can in turn be used as a probe to hybridize with DNA libraries obtained from related species. Specifically the *A. niger* acetyl xylan esterase gene isolated in one of the examples, was shown to hybridize with *T. reesei* chromosomal DNA.

In the examples the cloning and expression of a 3.4 kb Sst1 DNA fragment obtained from *Aspergillus niger* is demonstrated. The expression is performed using the complete gene in *A. niger*.

As described above acetyl xylan esterase can be used to deacetylate xylan. Since it was observed that the activity of acetyl xylan esterase as a single enzyme may lead to precipitation of the obtained polymer it is preferable to use the enzyme in conjunction with other xylan degrading enzymes such as xylanases, arabinofuranosidases, xylosidases and glucuronidases preferably selected from the group consisting of xylanase, a-arabinofuranosidase, β-xylosidase and αglucuronidase. In Example 5 the combined action of acetyl xylan esterase and β-(1,4)-xylanase and β-(1,4)-xylosidase respectively, is demonstrated.

Acetyl xylan esterases can preferably be used in processes wherein xylan has to be degraded. As a consequence of the deacylating reaction the xylan becomes better accessible for xylanases.

Specific applications of acetyl xylan esterases or combinations of this enzyme with other xylan degrading enzymes include;

the pretreatment of animal feed to increase the digestibility, addition of these enzymes to feed 'treatment in situ', treatment of fruit juices and beer in order to improve rheological characteristics and clarity, pulp and (waste-) paper processing in order to improve the process of bleaching and de-watering.

In general this enzyme or combinations of this enzyme with other enzymes can be used to degrade biological cell-wall material to increase digestibility or flow characteristics in industrial applications relating to the preparation of fruit juices or beer.

Another important aspect concerning the use of acetyl xylan esterase in feed is its effect on viscosity. Deacetylation of xylan decreases the solubility of the feed components and thereby the viscosity is diminished. This leads to an increased ease of handling, and a reduced anti-nutritional effect of the pentosanes. In accordance with this the present invention provides animal feed compositions containing acetyl xylan esterase.

Furthermore, the accesibility of xylan for xylanases is increased. This is important in the release of lignin from pulp. Generally kraft pulp is treated with xylanases in order to remove lignin in the preparation of paper products. Due to the high degree of acetylation of xylan xylanase is not optimally used. The effectivity of xylanases is greatly increased when pulp is treated with acetyl xylan esterase either before or at the same time as the xylanase treatment.

In accordance with the above the present invention provides a method for increasing feed digestibility characterized in that an effective amount of acetyl xylan esterase is added to the feed. The present invnention also provides a method for decreasing the viscosity of xylan containing compositions characterized in that an effective amount of acetyl xylan esterase is added. The present invention also provides a method for the release of lignin from kraft pulp in the preparation of paper products.

The following examples are offered by way of illustration and are not meant to limit the scope of the present invention in any way.

EXPERIMENTAL

Buffers and Stock Solutions

Appropriate stock solutions were used in the experiments described in the examples.

The following stock solutions were made according to Maniatis et al. ('Molecular Cloning' Cold Spring Harbor, 1982 and 1989, 2nd ed.); TE buffer, 20×SSC, Hybridization buffer, 100×Denhardt's solution, SM buffer, 50×TAE buffer, DNA loading buffer (xylene cyanol and bromophenol blue), NCZYM medium, LB medium. Ligation buffer was prepared as indicated by the supplier of the enzyme.

Further solutions contained the following components; 5×RNB per 1000 ml:

121.10 g Tris, 73.04 g NaCl, 95.10 g EGTA, pH 8.5
Visniac solution:

10 g EDTA, 4.4 g $ZnSO_4 \cdot 7H_2O$, 1.0 g $MnCl_2 \cdot 4H_2O$ 0.32 g $CoCl_2 \cdot 6H_2O$, 0.32 g $CuSO_4 \cdot 5H_2O$ 0.22 g $(NH_4)_6Mo_7O_{24} \cdot 4H_2O$, 1.47 g $CaCl_2 \cdot 2H_2O$ 1.0 g $FeSO_4 \cdot 7H_2O$, pH 4.0

(Visniac and Santer, 1957, Bact. Rev. 21: 195–213)
Minimal medium per 1000 ml:

6.0 g $NaNO_3$, 1.5 g $KH_2PO_4$, 0.5 g $MgSO_4 \cdot 7H_2O$ 0.5 g KCl, 1 ml Visniac solution Carbon source as indicated, pH 6.0
Strains used in the Examples:

*E. coli* JM101 (Yanisch-Perron et al., 1985, Gene 33: 103)

*E. coli* LE 392 (Murray, 1977, Mol. Gen. Genet. 150: 53–58)

*Aspergillus niger* N402 (Goosen et al., 1987, Curr. Genet. 11: 499–503)

*Aspergillus niger* N593 (Goosen et al., 1987, supra)
Vectors used in the Examples:

pUC9 (Vieirra and Messing, 1982, Gene 19: 259–268 and Yanisch-Perron et al., 1985)

M13mp18/M13mp19 (Messing, J., 1983, IOIC: 10–78, Norrander et al., 1983, Gene 26: 101–106)
Acetyl Esterase Assay The assay was as described by Biely et al. (1985, supra). Enzyme solution (10–50 μl) was mixed with 1 ml of a freshly prepared saturated solution of 4-nitrophenyl acetate (SIGMA) in 0.2M phospate buffer, pH 6.5 and incubated at 22° C. Liberation of 4-nitrophenol was followed photometrically at 410 nm as a function of time. One unit of acetyl esterase activity hydrolyzes 1 μmole of the substrate in 1 min.

Enzymes

The endo-(1,4)-β-xylanase I, II, III (E.C. 3.2.1.8) and the β-(1,4)-xylosidase (E.C. 3.2.1.37) were purified as described by Kormelink et al. (1990, In: Proc. 5th European Congress on Biomass and Bioenergy, Lissabon 9–13 October 1989). from *Aspergillus awamori* CMI 142717.

Combined Action of Acetyl Esterase and Xylan-Degrading Enzymes

The release of acetic acid and xylose oligomers was determined by HPLC after degradation of steamed birchwood xylan by single or combined actions of acetyl esterase and endo-(1,4)-β-xylanase I, endo-(1,4)-β-xylanase II, endo-(1,4)-β-xylanase III and β-(1,4)-xylosidase. A 0.2% (w/v) steamed birchwood xylan solution was incubated with 1.0 μg/ml acetyl esterase and 0.1 μg/ml endo-(1,4)-β-xylanase I, endo-(1,4)-β-xylanase II, endo-(1,4)-β-xylanase III or β-(1,4)-xylosidase at 30° C. The degradation was followed over a time range from 0–8 hours. The reaction was terminated by placing the sample for 5 minutes in a boiling water bath. Steamed birchwood was prepared as described by Puls et al. (1985, Appl. Microbiol. Biotechnol. 22: 416–423).

HPLC—Neutral Sugars

Neutral sugars released by the single and combined action of endo-(1,4)-β-xylanase I, II, III, β-(1,4)-xylosidase and acetyl esterase on steamed birchwood xylan were determined by HPLC. Samples were pretreated with $Pb(NO_3)_2$ according to Voragen et al. (1986, Food Hydrocolloids 1: 65–70) and injected on a CH-Pb column (Merck, Darmstadt, FRG) eluted with millipore water (0.4 ml/min) at 85° C. Sugars were detected by a Shodex SE-61 RI detector.

EXAMPLES

Example I

Purification and Characterization of *A. niger* Acetyl Xylan Esterase AXE I.

Example 1.1

Purification of *A. niger* Acetyl Xylan Esterase AXE I

After growth of *Aspergillus niger* DS16813 the culture was centrifuged and the supernatant was concentrated through ultrafiltration. A sample of 73 ml was applied to a DEAE-trisacryl (IBF) column (a XK 50 Pharmacia column filled with 400 ml of DEAE-trisacryl and buffered with Tris-HCl 0.05M, pH 7.8) and eluted with a linear gradient 0.0–1.0M NaCl in Tris-HCl 0.05M, pH 7.8. Fractions were assayed for acetyl esterase activity, as described above.

Fractions containing acetyl esterase activity were pooled and applied to a semi-preparative DEAE HPLC column (Waters DEAE 5 PW 21.5 mm×15 cm) equilibrated with phosphate 0.05M pH 7.5. Elution was with a linear 0.0–1.0M NaCl gradient in the same buffer. The final purification was performed with an analytical DEAE HPLC column (same as above but in this case 7.5 mm×7.5 cm) or using SDS-PAA gelelectrophoresis. The fractions obtained were used for amino acid sequencing as such or the protein was first digested with an appropriate proteolytic enzyme. In the latter case the peptides obtained were separated through HPLC, before amino acid sequencing was performed.

Example 1.2

Amino acid sequencing of N-terminal and internal peptides of acetyl xylan esterase Amino acid sequencing of the N-terminus of *A. niger* acetyl xylan esterase AXE I, using an Applied Biosystems gas phase sequencer, revealed the following sequence:

Ser-Gly-Ser-Leu-Gln-Gln-Val-Thr-Asp-Phe-Gly-Asp-Asn-Pro-Thr-Asn-Val-(Gly)-Met-Tyr-(Ile)     (Formula 1)

Amino acid sequence determination of CNBr peptides of acetyl xylan esterase AXE I, after separation using HPLC, revealed the following sequences:

CNBr peptide 1:

Tyr—Ile—Tyr—Val—Pro—Asn—Asn—Leu—Ala—Ser—Asn—Pro—Gly—Ile—Val—
Val—Ala—Ile—His—Tyr— (Formula 2)
CNBr peptide 2:

?-Ser—Gly—Tyr—Ser—Gly—Ser—Phe—Pro—Thr-?-Gln—(Ile)—Tyr—(His/
Thr)—(Ser)—Gly—(Ser)—(Ser)—Asp— (Formula 3)

Example 2

Screening of the *A. niger* genomic Library for the Acetyl Xylan Esterase Gene (axeA) and Isolation of the Gene.

Example 2.1

$^{32}$P-labeling of synthetic oligonucleotides

The amino acid sequence shown in Example 1.2 (Formula 1) was used to derive oligonucleotide mixes corresponding to the N-terminal amino acid sequence. The oligonucleotides were synthesized by the phosphoamidite method described by Crea et al. (1979, Tetrahedron Lett. 5: 395–398) using an Applied Biosystems oligonucleotide synthesizer.

The following oligonucleotide mixture was used;

| GGATTATCIC CAAAATCIGT IACCTGCTG | 29 | (Formula 4) |
|---|---|---|
| G G   G G | | | in a final concentration of 37 pmol oligonucleotides per µl. This oligonucleotide mixture was labeled in a reaction mixture of the following composition; 37 pmol oligonucleotide mixture, 66 mM Tris. HCl pH 7.6, 1 mM ATP, 1 mM spermidine, 10 mM MgCl$_2$, 15 mM dithiothreitol, 200 µg/ml BSA, 34 pmol $\tau^{32}$–P ATP (NEN, 6000 Ci/mMol) and 30 U T$_4$ polynucleotide kinase (BRL) in a final volume of 50 µl. The reaction was terminated by the addition of 4 µl 0.5M EDTA pH 8.0. The labeled oligonucleotide mixture was used without further purification in screening of the genomic library (Example 2.3) and in Southern blottings (Example 2.5 and 2.6).

Example 2.2

Construction of a Genomic Library of *Aspergillus niger* Strain DS16813 (CBS 323.90)

DNA from *Aspergillus niger* DS16813 (deposited at the Centraal Bureau voor Schimmelcultures, Baarn, The Netherlands on Jul. 20, 1990 (CBS 323.90)) was isolated using the procedure described by de Graaff et al. (1988, Curr. Genet. 13: 315–321). Briefly, mycelium, grown overnight was harvested and stored at –80° C. Nucleic acids were isolated by disrupting 0.5 g frozen mycelium using an microdismembrator (Braun). The mycelial powder was extracted with extraction buffer containing: 1 ml tri-isopropylnaphtalene sulfonic acid (TNS) (20 mg/ml), 1 ml p-aminosalicylic acid (PAS) (120 mg/ml) and 0.5 ml 5×RNB buffer and which was equilibrated with 1.5 ml phenol. The extraction buffer was added to the mycelium powder and a phenol/chloroform, chloroform extraction was performed. The DNA was subsequently isolated by ethanol precipitation. RNA was removed from the solution by treating with RNase A.

DNA, isolated from *Aspergillus niger* DS16813, as described above, was partially digested by Sau 3A. The resulting fragments were size fractionated by electrophoresis on 0.4% agarose in TAE. Fragments of 14 kb to 22 kb in size, were recovered from the gel by cutting the appropriate region from the gel and subsequent electroelution.

The fragments were ligated with bacteriophage lambda EMBL 3 Bam HI arms, obtained from Promega, using a standard procedure. The ligated DNA was packaged in vitro using Gigapack II Gold packaging extract (Stratagene) and plated on *E. coli* LE392 using NZYCM medium according to the manufacturer's instructions.

The primary library thus obtained was titrated and amplified. A phage stock was made containing approximately $10^{10}$ pfu/ml.

Example 2.3

Screening of the *A. niger* Genomic Library for the axeA Gene.

A genomic library of *A. niger* was constructed as described above. For obtaining the axeA gene, 3×10$^3$ pfu per plate are plated in NZYCM topagarose containing 0.7% agarose on four 85-mm-diameter NZYCM (1.2% agar) plates as described (Maniatis et al., 1982, supra, pp. 64), using *E. coli* LE392 as plating bacteria.

After overnight incubation of the plates at 37° C. two replicas of each plate were made on HybondN$^+$ filters (Amersham) as described in Maniatis et al. (1982, supra, pp. 320–321).

After wetting the filters in 3×SSC, the filters were washed for 60 min. at room temperature in 3×SSC. The filters were prehybridized at 65° C. for two hours in prehybridization buffer containing; 6×SSC, 0.5% SDS, 10×Denhardt's solution and 100 µg/ml heat denatured herring sperm DNA (Boehringer Mannheim). After two hours of prehybridization the buffer was replaced by hybridization buffer which is identical to the prehybridization buffer, except that this buffer does not contain herring sperm DNA, but contains $^{32}$–P labeled oligonucleotide mix Formula 1, prepared as described in Example 2.1. The filters were hybridized for 18 hrs at a final temperature of 47° C., slowly, reached from the initial temperature of 65° C.

After hybridization the filters were first washed in 2×SSC, after which the filters were washed in prewarmed hybridization buffer at 47° C. Finally the filters were washed twice for 30 min. at 56° C. in 6×SSC, 0.05% sodium pyrophosphate. The air dried filters were taped on a sheet of Whatman 3 MM paper, keying marks were made with radioactive ink and the Whatman paper and filters covered with Saran Wrap. Hybridizing plaques were identified by exposure of Kodak XAR X-ray film for 72 hrs at –70° C. using an intensifying screen.

Seven hybridizing plaques, were identified and named lambda$_{axe1}$ to lambda$_{axe7}$. Each positive plaque was picked from the plate using a Pasteur pipette and the phages were eluted from the agar plug in 1 ml of SM buffer containing 20 µl chloroform, as described in Maniatis et al. (1982, supra, pp. 64). The phages obtained were purified by repeating the procedure described above using filter replicas from plates containing 50-100 plaques of the isolated phages.

After purification the phages were propagated by plating $5 \times 10^3$ phages on NZYCM medium. After overnight incubation at 37° C. confluent plates were obtained, from which the phages were eluted by adding 5 ml SM buffer and storing the plate for 2 hrs at 4° C. with intermittent shaking. After collection of the supernatant using a pipette, the bacteria were removed from the solution by centrifugation at 4,000×g for 10 min. at 4° C. To the supernatant 0.3% chloroform was added and the number of pfu determined. These phage stocks contain approximately $10^{10}$ pfu/ml.

Example 2.4

Isolation of DNA from bacteriophage lambda.

Each of the isolated phages were propagated by combining $5*10^9$ E. coli LE392 bacteria in 300 μl SM buffer with $2*10^6$ pfu for 15 min. After incubation the infected bacteria were used to inoculate 100 ml prewarmed (37° C.) NZYCM medium and subsequently incubated for 9-12 hrs at 37° C. in a New Brunswick rotation shaker at 250 rpm, after which period the bacteria were lysed. The bacterial debris was removed by centrifugation for 10 min. at 10 krpm. at 4° C., in a Sorvall High Speed centrifuge. The phages were precipitated from the supernatant obtained (100 ml) by the addition of 10 g polyethyleneglycol-6000 and 11.7 g NaCl and storing the solution overnight at 4° C. The precipitated phages were collected by centrifugation at 14,000×g at 4° C. for 20 min. The supernatant was removed by aspiration, while the rest of the liquid was removed using a paper towel. The phages were carefully resuspended in 4 ml SM buffer and extracted once with an equal volume of chloroform.

Before the DNA was extracted from the phage particles, DNA and RNA originating from the lysed bacteria was removed by incubation of the phage suspension with DNase I and RNase A (both 100 μg/ml) for 30 min. at 37° C. The phage DNA was subsequently released from the phages by the addition of EDTA to a final concentration of 20 mM while the protein was removed from the solution by extracting twice with an equal volume phenol/chloroform/isoamyl alcohol (25:24:1). After separation of the phases by centrifugation using a Sorvall centrifuge (14,000×g, 10 min.), the aqueous phase was extracted once with an equal volume chloroform/isoamylalcohol (24:1). The phases were separated by centrifugation after which the DNA was precipitated from the aqueous phase by the addition 0.1 vol. 5M sodiumperchlorate and 0.1 vol. isopropanol and incubation on ice for 30 min. The DNA was recovered by centrifugation for 10 min. at 4° C. (14,000×g). The supernatant was removed by aspiration after which the DNA was resuspended in 400 μl TE buffer. The DNA was precipitated once again from this solution by the addition of 0.1 vol. 3M sodium acetate and 2 vol. ethanol. The DNA was collected by centrifugation for 10 min. at 4° C. (14,000×g). The supernatant was removed by aspiration, the remaining pellet was briefly dried under vacuum, after which the DNA was resuspended in 125 μl TE buffer containing 0.1 μg/ml RNase A. This purification procedure results in the isolation of approximately 50-100 μg DNA from each phage.

Example 2.5

Restriction analysis of axeA containing phages.

The isolated DNA of phages lambda$_{axe1}$ to lambda$_{axe7}$ was analyzed by Southern analysis using the following restriction enzymes; ECoRI; HinDIII; SphI and HinCII. The DNA was digested for 3 hrs at 37° C. in a reaction mixture composed of the following solutions; 5 μl (≈1 μg) DNA solution; 2 μl of the appropriate 10×Reaction buffer (BRL); 10 U Restriction enzyme (BRL) and sterile distilled water to give a final volume of 20 μl. After digestion the DNA was precipitated by the addition of 0.1 vol. 3M NaAc and 2 vol. ethanol. The DNA was collected by centrifugation for 10 min. at room temperature (14,000×g). The supernatant was removed by aspiration, the remaining pellet was briefly dried under vacuum and resuspended in sterile distilled water. After addition of 4 μl DNA loading buffer the samples were incubated for 10 min. at 65° C. and rapidly cooled on ice, before loading the samples on a 0.6% agarose gel in TAE buffer. The DNA fragments were separated by electrophoresis at 25 V for 15-18 hrs.

After electrophoresis the DNA was transferred and denatured by alkaline vacuum blotting (VacuGene XL, Pharmacia LKB) to nylon membrane (Gene Bind 45, Pharmacia LKB) as described in the instruction manual (pp. 25-26) and subsequently prehybridized and hybridized using the labeled oligonucleotide mixture Formula 1 as described in Example 2.1 and hybridization conditions as described in Example 2.2. The hybridization pattern was obtained by exposure of Kodak XAR-5 X-ray film for 18 hrs at −70° C. using an intensifying screen.

From the results obtained it is concluded that the DNA of five out of-the seven isolated clones hybridize with the oligonucleotide mixture derived from the N-terminal amino acid sequence. In all five clones fragments originating from the same genomic region were found. In a more extensive Southern analysis, using the enzymes BglII, EcoRV, NCoI, PstI, SstI and XbaI, a partial restriction map of this genomic region was constructed. From this experiment it is concluded that a 3.4 kb SstI fragment contains the A. niger axeA gene.

Example 2.6

Subcloning of the A. niger axeA Gene.

From phage lambda$_{axe3}$ the 3.4 kb SstI fragment was isolated by digesting the phage DNA with SstI and separation of the fragments as described in Example 2.4. The fragment was cut from the agarose gel, after which it was recovered from the piece of agarose by electroelution using ISCO cups. Both on the large and the small container of this cup a dialysis membrane was mounted, the cup was filled with 0.005×TAE and the piece of agarose is placed in the large container of the cup. Subsequently the cup was placed in the electro-elution apparatus, with the large container in the cathode chamber containing TAE and the small container at the anode chamber containing TAE/3M NaCl. The fragments were electro-eluted at 100 V during 2 hrs. After this period the cup was taken from the electro-elution apparatus and the buffer was removed from the large container, while from the small container the buffer was only removed from the upper part. The remaining buffer (200 μl) containing the DNA fragments was dialyzed in the cup against distilled water during 30 min. Finally the DNA was precipitated by the addition of 0.1 vol. 3M NaAc, pH 5,6 and 2 vol. cold (−20° C.) ethanol. The DNA was collected by centrifugation (Eppendorf centrifuge) for 30 min. at 14,000×g. at 4° C. After removal of the supernatant the DNA pellet was dried using a Savant Speedvac vacuumcentrifuge. The DNA was dissolved in 10 μl TE buffer and the concentration determined by agarose electrophoresis, using Lambda DNA with a known concentration as a reference and ethidiumbromide staining to detect the DNA.

The fragment obtained was ligated in the vector pEMBL18 digested with SstI and dephosphorylated with alkaline phosphatase prepared as follows; 1 µl (1 µg/µl) pEMBL18 was mixed with 2 µl 10×React 10 (BRL), 1 µl (1 U/µl) SstI and 16 µl sterile distilled water. The DNA was digested for 1 hr at 37° C., after which 0.5 µl alkaline phosphatase (1 U/µl (Pharmacia LKB) was added followed by further incubation at 37° C. for another 30 min. The linearized vector was isolated from a 0.6% agarose gel as described above.

The 3.4 kb SstI fragment was ligated in the vector resulting in the plasmid pIM150, by the following procedure. 100 ng pEMBL18 fragment was mixed with 100 ng 3.4 kb SstI fragment and 4 µl 5*ligation buffer (composition; 500 mM Tris-HCl, pH 7.6; 100 mM $MgCl_2$; 10 mM ATP; 10 mM dithiotreitol; 25% PEG-6000) and 1 µl (1.2 U/µl) DNA ligase (BRL) was added to this mixture in a final volume of 20 µl. After incubation for 16 hrs at 14° C. the mixture was diluted to 100 µl with sterile water. 10 µl of the diluted mixture was used to transform E. coli JM101 competent cells, prepared by the CM1, CM2 method as described in the Pharmacia Manual for the M13 cloning/sequencing system. A selection of six of the resulting colonies were grown overnight in LB medium containing 100 µg/ml ampicillin. From the cultures plasmid DNA was isolated by the alkaline lysis method as described by Maniatis et al. (1982, pp. 368–369), which was used in restriction analysis, as described in Example 2.4 to select a clone harboring the desired plasmid. Plasmid DNA was isolated on a large scale from 500 ml cultures E. coli JM101 containing the plasmid pIM150 grown in LB medium containing 100 µg/ml ampicillin (Maniatis et al., 1982, p 86). The plasmid was purified by CsCl centrifugation, phenolized, ethanol precipitated and dissolved in 400 µl TE. The yield was approximately 500 µg.

Figure 1:
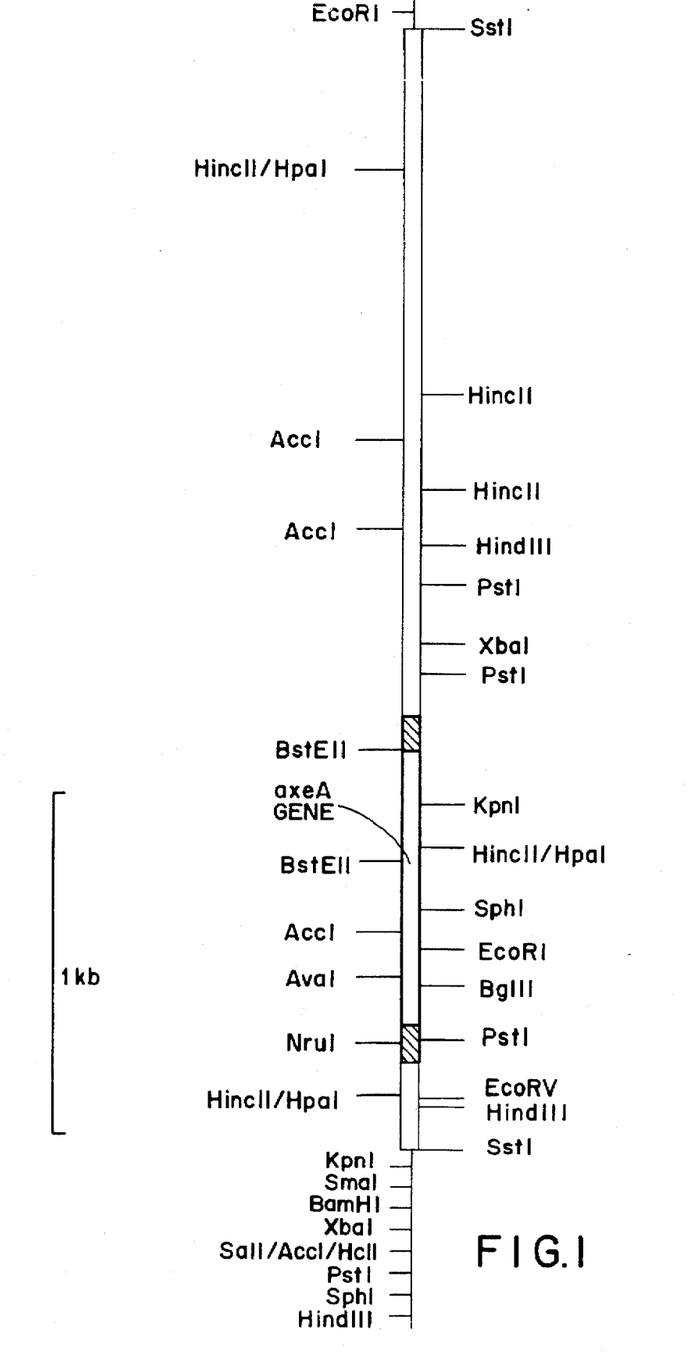
FIG. 1 shows the restriction map of a 3.4 kb Sst1 DNA fragment containing the *Aspergillus niger* axeA gene.

The plasmid pIM150 was further analyzed by restriction enzymes resulting in the restriction map shown in FIG. 1. This plasmid was deposited with the Centraal Bureau voor Schimmelcultures (CBS) in Baarn, the Netherlands. In E. coli DH5α on Mar. 11 1991, under number CBS 157.91.

Example 3

Sequence Determination of the A. niger axeA Gene

The sequence of the A. niger axeA gene, its promoter-regulation region, the structural part of the gene and the termination region, was determined by subcloning fragments from pIM150 in M13mp18/mp19, in combination with the use of specific oligonucleotides as primers in the sequencing reactions.

For nucleotide sequence analysis restriction fragments were isolated as described in Example 2.5 and cloned in bacteriophage M13 mp18/19 RF DNA vectors (Messing 1983, supra; Norrander et al., supra, 1983), digested with the appropriate restriction enzymes, as described in Example 2.5. The nucleotide sequences were determined by the dideoxynucleotide chain termination procedure (Sanger et al., 1977, Proc. Natl. Acad. Sci. USA 74: 5463–5467) using the Pharmacia $T_7$ DNA polymerase sequencing kit. Computer analysis was done using the PC/GENE program. The sequence determined is given as SEQ ID NO:7 (in the Sequence Listing). The position of the introns was derived based on the consensus sequences for 5' and 3' splice sites.

Example 4

Expression of the cloned axeA gene in A. niger N593

Example 4.1

Introduction of the aXeA gene in A. niger N593 by cotransformation.

The plasmid pIM150, obtained in Example 2.5 was introduced in A. niger by cotransformation of A. niger N593 (a pyr⁻ mutant of A. niger N402) using the A. niger pyrA as a selective marker on the plasmid pGW635 (Goosen et al., 1989, Mol. Gen. Genet. 219: 282–288) and the plasmid pIM150 as the cotransforming plasmid.

Protoplasts were prepared from mycelium by growing A. niger N593 on minimal medium supplemented with 0.5% yeast extract, 0.2% casamino acids, 50 mM glucose and 10 mM uridine for 20 hrs at 30° C. The preparation of protoplasts of A. niger N593 and the transformation procedure was performed as described by Goosen et al., 1987 (supra). The resulting PYR⁺ transformants were analyzed for the expression of the axeA gene by Western blot analysis.

Example 4.2

Screening of transformants for the expression of the axeA gene

The transformants obtained in Example 4.1 were analyzed for the formation of the axeA gene product, the AXE I protein. Twenty transformants were selected and grown for 72 hrs on medium containing per 1; 30 g birch wood xylan (Roth); 6 g NaNO3, 0,5 g KCl, 0,5 g $MgSO_4·7H_2O$, 0.5 g $CaCl_2$, 1,5 g KH2PO., and 0,1 g yeast extract and 1 ml/l Visniac solution (pH 6.0). After growth the mycelium was removed by filtration and the culture filtrate was analyzed by SDS-polyacrylamide gel electrophoresis, using a gel containing 12% acrylamide. The AXE I protein was detected on nitrocellulose after electroblotting and incubation with polyclonal antibodies raised against the AXE I protein purified as described in Example 1.1. The antibody bound, was detected after incubation with goat-anti-rabbit antibody conjugated to alkaline phosphatase, according to the Biorad instruction manual.

Four of the twenty transformants analyzed overproduced the AXE I protein as detected by this procedure. The protein was secreted into the medium. Of the transformants analyzed one was selected for giving the highest yields of the AXE I protein, transformant TrA10.

Example 5

Figure 2:
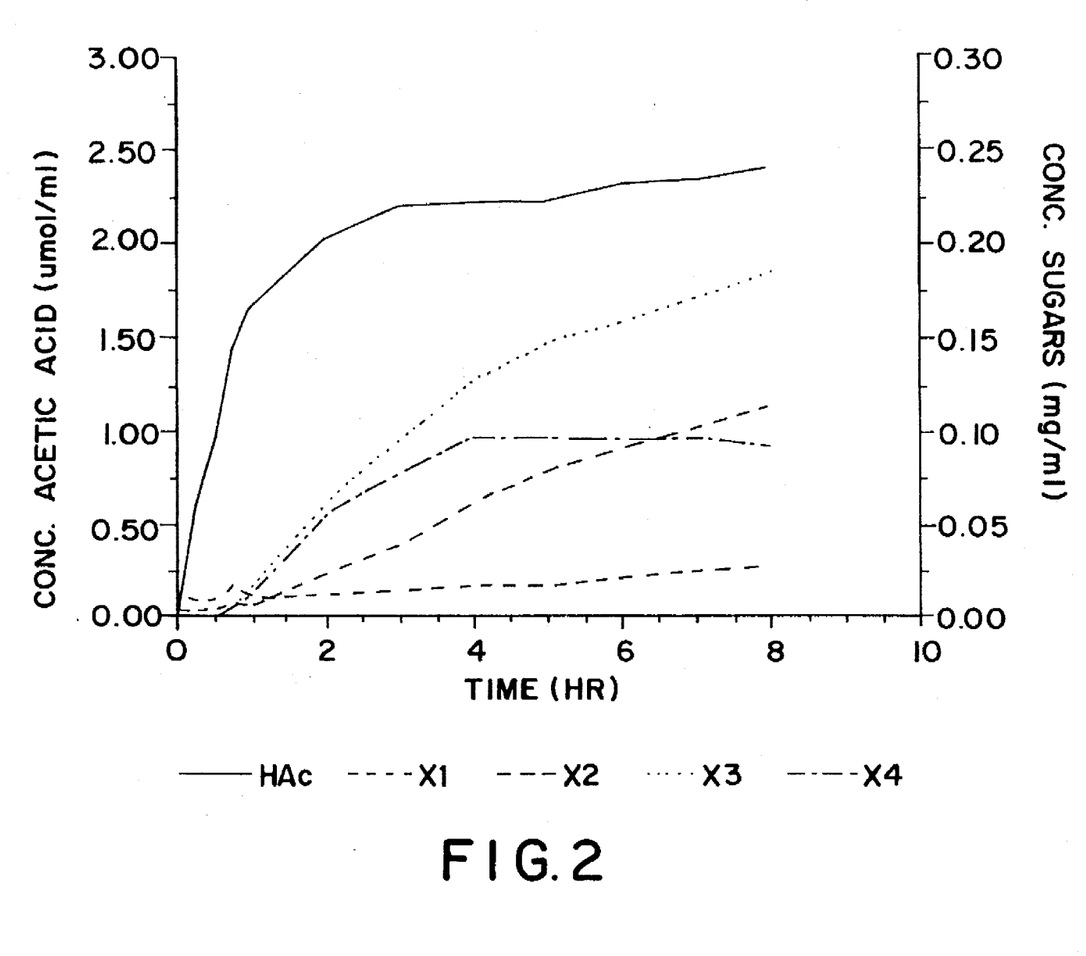
FIG. 2 shows the release of acetic acid (HAc) and xylose oligomers ($X_1$, $X_2$, $X_3$ and $X_4$) from a 0.2% (w/v) steamed birchwood xylan solution by the combined action of acetyl esterase (1 µg/ml) and endo-(1,4)-β-xylanase I (0.1 µg/ml).

Combined action of acetyl xylan esterase and endo-(1,4)-β-xylanase and β-(1,4)-xylosidase respectively A 0.2% (w/v) steamed birchwood xylan solution was incubated with acetyl esterase and combinations of acetyl esterase and endo-(1,4)-β-xylanase I, endo-(1,4)-β-xylanase II, endo-(1,4)-β-xylanase III or β-(1,4)-xylosidase in time. Time curves (as shown for endo-(1,4)-β-xy;lanase in FIG. 2) show that endo-(1,4)-β-xylanase I, II and III start releasing significant amounts of xylose and xylose oligomers (X2, X3 and X4) only after most of the acetyl groups have been released. The acetyl esterase does not release more acetic acid than when used in combination with xylan-degrading enzymes. The release of xylose by β-(1,4)-xylosidase from steamed birchwood xylan is slowly but steady. Without acetyl xylan esterase, the endo-(1,4)-β-xylanases and the β-(1,4)-xylosidase do not degrade the steamed birchwood xylan i.e. they do not release significant amounts of X1, X2, X3 and X4. The acetyl groups may therefore block the enzyme activity of the endo-(1,4)-β-xylanases or β-(1,4)-xylosidase activity.

To emphasize the degradation of the steamed birchwood xylan, comparative studies were carried out by incubation of a steamed birchwood xylan for 24 hrs with only acetyl esterase, endo-(1,4)-β-xylanase I, endo-(1,4)-β-xylanase II, endo-(1,4)-β-xylanase III or β-(1,4)-xylosidase, and with combinations of acetyl esterase and these xylan-degrading enzymes. Also pre-incubations with acetyl esterase for 1 hr followed by 1 and 24 hrs incubations with the xylan-degrading enzymes were carried out. Table 1 shows the results of the release of acetic acid, xylose, and xylose oligomers after 24 hours of incubation.

The acetyl xylan esterase releases 2.60–2.80 and 4.30 μmol/ml of acetyl groups after 1 and 24 hrs respectively (4.30 μmol/ml equals 80–90% release of all the acetyl groups). There is no increase in the initial rate for the release of acetic acid by using the combination of xylan-degrading enzymes and acetyl xylan esterase.

Without acetyl xylan esterase, the endo-(1,4)-β-xylanases and β-(1,4)-xylosidase from A. awamori release no or only traces of xylose oligomers from steamed birchwood xylan (i.e. $X_1$ or $X_1$, $X_2$, and $X_3$, by β-(1,4)-xylosidase and endo-(1,4)-β-xylanase I respectively). In combination with acetyl xylan esterase, these xylan-degrading enzymes release reasonable amounts of xylose oligomers after 24 hrs of incubation. However, by pretreating the steamed birchwood xylan with acetyl esterase for only 1 hr, the amount of xylose oligomers is somewhat lower. The combination of acetyl xylan esterase and xylan-degrading enzymes thus releases the highest amount of $X_1$, $X_2$, $X_3$, and $X_4$. This discrepancy may be explained by a linearization of the xylose oligomers by deacylation of the steamed birchwood xylan. If not degraded into smaller oligomers by the xylan-degrading enzymes, the higher xylose oligomers may aggregate as a result of this linearization and cause a precipitate. This precipitate is less accessible for degradation (Poutanen et al, 1989 and 1990).

From the results presented here, it is clear that by the initial release of acetyl groups by the acetyl esterase, new sites have been created on the polysaccharide backbone suitable for the binding of endo-(1,4)-β-xylanase. The fact that the purified xylan-degrading enzymes from A. awamori did not degrade the steamed birchwood xylan significantly, coincides with the findings of Poutanen et al. (supra) that a crude preparation of A. awamori did not degrade steamed birchwood xylan significantly.

TABLE 1

Release of acetic acid, xylose and xylose oligomers from a 0.2% (w/v) steamed birchwood xylan solution by the single and combined action of 1.0 μg/ml acetyl esterase and 0.1 μg/ml endo-β-(1,4)-D-xylanase I, endo-β-(1,4)-D-xylanase II, endo-β-(1,4)-D-xylanase III or β-(1,4)-xylosidase.

| Type of incubation | Product formation | | | | |
|---|---|---|---|---|---|
| | Acetic acid[1] | $X^2$ | $X2^2$ | $X3^2$ | $X4^2$ |
| Blanc | 0.0 | 0.008 | 0.002 | 0.003 | 0.000 |
| AE | 4.30 | | | | |

TABLE 1-continued

Release of acetic acid, xylose and xylose oligomers from a 0.2% (w/v) steamed birchwood xylan solution by the single and combined action of 1.0 μg/ml acetyl esterase and 0.1 μg/ml endo-β-(1,4)-D-xylanase I, endo-β-(1,4)-D-xylanase II, endo-β-(1,4)-D-xylanase III or β-(1,4)-xylosidase.

| Type of incubation | Product formation | | | | |
|---|---|---|---|---|---|
| | Acetic acid[1] | $X^2$ | $X2^2$ | $X3^2$ | $X4^2$ |
| Endo I | 0.06 | 0.022 | 0.27 | 0.079 | 0.000 |
| Endo II | 0.12 | 0.010 | 0.011 | 0.011 | 0.000 |
| Endo III | 0.02 | 0.010 | 0.010 | 0.011 | 0.000 |
| β-xylosidase | 0.16 | 0.065 | 0.000 | 0.000 | 0.000 |
| AE + Endo I | 4.30 | 0.043 | 0.210 | 0.265 | 0.048 |
| AE + Endo II | 4.30 | 0.010 | 0.104 | 0.252 | 0.105 |
| AE + Endo III | 4.30 | 0.020 | 0.209 | 0.222 | 0.054 |
| AE + β-xylosidase | 4.30 | 0.237 | 0.006 | 0.007 | 0.006 |
| AE[3] + Endo[4] I | 2.64 | 0.036 | 0.149 | 0.253 | 0.063 |
| AE[3] + Endo[4] II | 2.76 | 0.010 | 0.038 | 0.080 | 0.045 |
| AE[3] + Endo[4] III | 2.55 | 0.012 | 0.067 | 0.077 | 0.042 |
| AE[3] + β-xylosidase[4] | 2.99 | 0.113 | 0.005 | 0.005 | 0.000 |

[1] μmol/ml
[2] mg/ml
[3] Pre-incubation 1 hr
[4] Pre-incubation 24 hrs

Example 6

In vitro test of acetyl xylan esterase activity under conditions simulating the digestive tract of poultry 1.1 grams of feed or feed components (with or without acetyl xylan esterase) was incubated for 1 hour in 50 mM sodium acetate buffer pH 5.5 at 39° C., simulating chicken's crop. After lowering the pH to 3.0 with HCl and addition of 5 ml of a pepsin solution (Merck: 5.28 g/l) the mixture was incubated for 1.5 hours at 39° C. as in the stomach. The small intestine of birds was simulated by raising the pH to 6.5 by the addition of sodium phosphate (2.5 ml 1M) and 2.5 ml pancreatine/bile acids. After another 1.5 hours incubation at 39° C. the mixture was centrifuged, the pellet was dried and its weight determined. The difference between the weights of the pellets of treated and untreated material was a measure for enzymatic activity under the standard conditions.

As examples of feed constituents wheat bran and maize meal were incubated with acetyl xylan esterase, according to the description given above. The dry matter digestibility was improved by several percents.

This indicates that acetyl xylan esterase can be used in the degradation of other than wood-borne hemicellulose material.

We claim:

1. An isolated and purified DNA molecule which comprises a nucleotide sequence encoding a protein having acetyl xylan esterase activity, which nucleotide sequence.
   (a) encodes the protein comprising the amino acid sequence of positions 26–304 in SEQ ID NO:8; or
   (b) encodes a modified protein which differs by one or more amino acids from positions 26–304 of SEQ ID NO:8 having acetyl xylan esterase activity that is encoded by a nucleotide sequence which hybridizes with the nucleotide sequence of SEQ ID NO:7 under the hybridization conditions of a hybridization buffer which is 6×SSC, 0.5% SDS and 10×Denhardt's at a starting temperature of 65° C. and a final temperature of 47° C. followed by washing in 2×SSC, followed by washing in said hybridization buffer at 47° C. followed by two washes for 30 minutes at 56° C. in 6×SSC, 0.05% pyrophosphate.

2. An expression system for the expression of a nucleotide sequence encoding a protein having acetyl xylan esterase activity, which encoding nucleotide sequence is operably linked to expression regulating sequences;
   (a) wherein said encoding nucleotide sequence encodes the protein which comprises the amino acid sequence shown as positions 26–304 in SEQ ID NO:8; or
   (b) wherein said encoding nucleotide sequence encodes a modified protein which differs by one or more amino acids from positions 26–304 of SEQ ID NO:8 having acetyl xylan esterase activity that is encoded by a nucleotide sequence that hybridizes to the nucleotide sequence of SEQ ID NO:7 under hybridization conditions of hybridization buffer which is 6×SSC, 0.5% SDS and 10×Denhart's at a starting temperature of 65° C. and a final temperature of 47° C. followed by washing in 2×SSC, followed by washing in said hybridization buffer at 47° C. followed by two washes for 30 minutes at 56° C. in 6×SSC, 0.05% pyrophosphate.

3. The expression system of claim 2 wherein the regulating sequences are heterologous with respect to the encoding nucleotide sequence.

4. A microbial host cell modified to contain the expression system of claim 2.

5. The modified microbial host cell of claim 4 wherein the host cell is an Aspergillus, a Bacillus or a Kluyveromyces.

6. A method for obtaining a protein having acetyl xylan esterase activity comprising:
   a) culturing the microbial host of claim 4 under conditions that give rise to the production of acetyl xylan esterase, and
   b) optionally recovering the acetyl xylan esterase from the culture.

7. The DNA molecule of claim 1 wherein said encoding nucleotide sequence encodes the amino acid sequence of positions 26–304 of SEQ ID NO:8.

8. The expression system of claim 2 wherein said encoding nucleotide sequence encodes the amino acid sequence of positions 26–304 of SEQ ID NO:8.

9. The method of claim 6 wherein said encoding nucleotide sequence encodes the amino acid sequence of positions 26–304 of SEQ ID NO:8.

10. The DNA molecule of claim 1 wherein
 (a) said encoding nucleotide sequence is that shown in SEQ ID NO:7 as encoding the amino acid sequence of positions, 26–304 or
 (b) said encoding nucleotide sequence encodes a protein indigenous to a fungus.

11. The expression system of claim 2 wherein the encoding nucleotide sequence
 (a) said encoding nucleotide sequence is that shown in SEQ ID NO:7 as encoding the amino acid sequence of positions 26–304, or
 (b) said encoding nucleotide sequence encodes a protein indigenous to fungus.

12. The method of claim 6 wherein the encoding nucleotide sequence
 (a) said encoding nucleotide sequence is that shown in SEQ ID NO:7 as encoding the amino acid sequence of positions 26–304, or
 (b) said encoding nucleotide sequence encodes a protein indigenous to a fungus.

13. The method of claim 12 wherein the fungus is selected from the group consisting of the genera Aspergillus, Trichoderma, and Schizophyllum.

14. The DNA molecule of claim 13 wherein the fungus is selected from the group consisting of the species *Trichoderma reesei, Aspergillus niger* and *Schizophyllum commune.*

15. A recombinant host cell modified to contain the expression system of claim 8.

16. A recombinant host cell modified to contain the expression system of claim 11.

* * * * *